United States Patent [19]

Bundy

[11] 4,097,505

[45] Jun. 27, 1978

[54] CIS-13-9-DEOXY-PGF$_2$ ANALOGS

[75] Inventor: Gordon L. Bundy, Portage, Mich.

[73] Assignee: The Upjohn Company, Kalamazoo, Mich.

[21] Appl. No.: 786,701

[22] Filed: Apr. 11, 1977

Related U.S. Application Data

[62] Division of Ser. No. 614,243, Sep. 17, 1975, Pat. No. 4,033,989.

[51] Int. Cl.$^2$ ........................................... C07C 177/00
[52] U.S. Cl. ................................. 260/413; 260/410; 260/410.5; 260/514 D; 260/410.9 R; 560/121
[58] Field of Search ............. 260/410, 410.5, 410.9 B, 260/413, 514 P; 560/121

[56] References Cited

U.S. PATENT DOCUMENTS 3,894,009  7/1975  Sakai ..................................... 260/240

Primary Examiner—Robert Gerstl
Attorney, Agent, or Firm—Robert A. Armitage

[57] ABSTRACT

Prostaglandin analogs with the following cyclopentane ring structure:

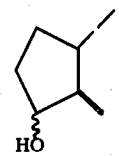

are disclosed along with intermediates useful in their preparation and processes for their preparation. These analogs are useful for some of the same pharmacological purposes as the prostaglandins.

27 Claims, No Drawings

CIS-13-9-DEOXY-PGF₂ ANALOGS

The present application is a divisional application of Ser. No. 614,243, filed Sep. 17, 1975, now issued as U.S. Pat. No. 4,033,989 on Jul. 5, 1977.

The present invention relates to prostaglandin analogs for which the essential material constituting a disclosure therefor is incorporated by reference here from U.S. Pat. No. 4,033,989, issued July 5, 1977.

What is claimed is:

1. A prostaglandin analog of the formula

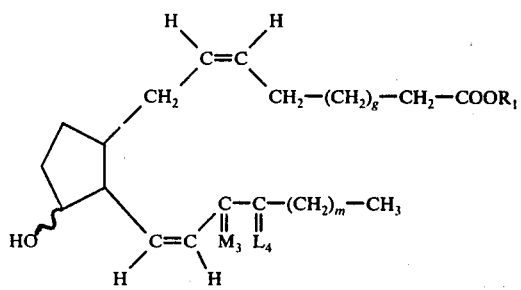

wherein $m$ is one to 5, inclusive;
wherein $M_3$ is

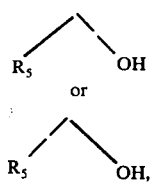

or

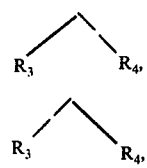

wherein $R_5$ and $R_6$ ae hydrogen or methyl, with the proviso that one of $R_5$ and $R_6$ is methyl only when the other is hydrogen;
wherein $L_4$ is

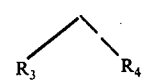

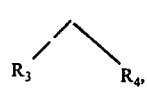

or a mixture of

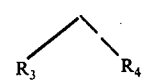

and

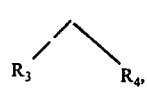

wherein $R_3$ and $R_4$ are hydrogen or methyl, being the same or different, with the proviso that one of $R_3$ and $R_4$ is methyl;
wherein $R_1$ is hydrogen, alkyl or one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and
wherein $g$ is one, 2, or 3.

2. A compound according to claim 1, wherein $M_1$ is

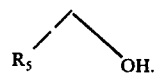

3. A compound according to claim 1, wherein $M_1$ is

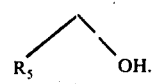

4. A compound according to claim 3, wherein m is 3.
5. A compound according to claim 4, wherein g is 3.
6. 2a,2b-Dihomo-15-epi-16,16-dimethyl-cis-13-9-deoxy-PGF₂, a compound according to claim 5.
7. A compound according to claim 4, wherein g is one.
8. 15-epi-16,16-Dimethyl-cis-13-9-deoxy-PGF₂, a compound according to claim 7.
9. 15-epi-16,16-Dimethyl-cis-13-9-deoxy-PGF₂, methyl ester, a compound according to claim 7.
10. A prostaglandin analog of the formula

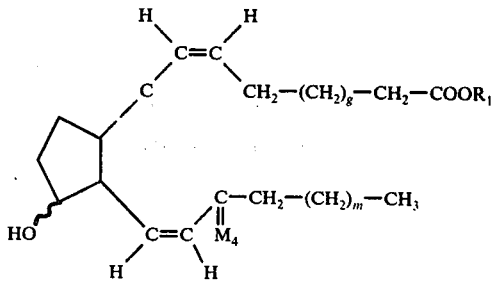

wherein $m$ is one to 5, inclusive;
wherein $M_4$ is

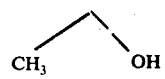

or

wherein $R_1$ is hydrogen, alkyl or one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharamacologically acceptable cation; and wherein $g$ is one, 2, or 3.

11. A compound according to claim 10, wherein $M_4$ is

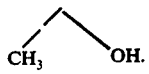

12. A compound according to claim 10, wherein $M_4$ is

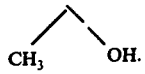

13. A compound according to claim 12, wherein $m$ is 3.

14. A compound according to claim 13, wherein $g$ is 3.

15. 2a,2b-Dihomo-15-epi-15-methyl-cis-13-9-deoxy-PGF$_2$, a compound according to claim 14.

16. A compound according to claim 13, wherein $g$ is one.

17. 15-epi-15-Methyl-cis-13-9-deoxy-PGF$_2$, a compound according to claim 16.

18. 15-epi-15-Methyl-cis-13-9-deoxy-PGF$_2$, methyl ester, a compound according to claim 16.

19. A prostaglandin analog of the formula

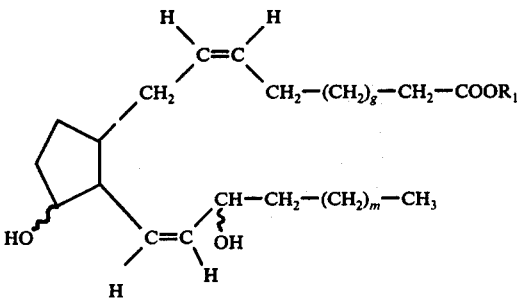

wherein $m$ is one to 5, inclusive;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and wherein $g$ is one, 2, or 3.

20. A compound according to claim 19, wherein $\sim$OH is $\beta$-OH.

21. A compound according to claim 19, wherein $\sim$OH is $\alpha$-OH.

22. A compound according to claim 21, wherein $m$ is 3.

23. A compound according to claim 22, wherein $g$ is 3.

24. 2a,2b-Dihomo-15-epi-cis-13-9-deoxy-PGF$_2$, a compound according to claim 23.

25. A compound according to claim 22, wherein $g$ is one.

26. 15-epi-cis-13-9-Deoxy-PGF$_2$, a compound according to claim 25.

27. 15-epi-cis-13-9-Deoxy-PGF$_2$, methyl ester, a compound according to claim 25.

* * * * *